United States Patent [19]

Ray

[11] Patent Number: 5,470,333
[45] Date of Patent: Nov. 28, 1995

[54] SYSTEM FOR STABILIZING THE CERVICAL AND THE LUMBAR REGION OF THE SPINE

[75] Inventor: R. Charles Ray, Tacoma, Wash.

[73] Assignee: Danek Medical, Inc., Memphis, Tenn.

[21] Appl. No.: 75,239

[22] Filed: Jun. 10, 1993

Related U.S. Application Data

[63] Continuation-in-part of Ser. No. 31,374, Mar. 11, 1993, abandoned.

[51] Int. Cl.[6] .................................................. A61B 17/70
[52] U.S. Cl. .................................. 606/61; 606/69; 606/71
[58] Field of Search ............................... 606/61, 60, 69, 606/71, 105, 72, 73

[56] References Cited

U.S. PATENT DOCUMENTS

| | | | |
|---|---|---|---|
| 1,025,008 | 4/1912 | Miner | 606/71 |
| 3,604,414 | 9/1971 | Borges | 606/71 |
| 4,246,660 | 1/1981 | Wevers | 606/71 |
| 5,084,049 | 1/1992 | Asher et al. | 606/61 |
| 5,092,893 | 3/1992 | Smith | 623/17 |
| 5,102,412 | 4/1992 | Rogozinski | 606/61 |
| 5,108,395 | 4/1992 | Laurain | 606/61 |
| 5,147,360 | 9/1992 | Dubousset | 606/61 |
| 5,261,907 | 11/1993 | Vignaud et al. | 606/60 |
| 5,261,909 | 11/1993 | Sutterlin et al. | 606/61 |

FOREIGN PATENT DOCUMENTS

| | | | |
|---|---|---|---|
| 1711860 | 2/1992 | U.S.S.R. | 606/61 |
| 780652 | 8/1957 | United Kingdom | 606/61 |

OTHER PUBLICATIONS

"Chopin Plate," Cotrel–Dubousset Instrumentation, SOFA-MOR, 6 pp. date unknown, author unknown.
"Triangulation of Pedicular Instrumentation," Ruland et al. vol. 16 No. 6 Supplement, 1991, S270–S276, Spine.

Posterior Cervical Stablization with Lateral Mass Plate Technique, Haid et al., p. 11, AME, Inc. Surgical Manual, date unknown.

"Lateral Mass Posterior Plating and Facet Fusion for Cervical Spine Instability," BNI Quarterly, vol. 7, No. 2, Spring 1991, p. 6. Author unknown.

"The TSRH™ System: designed with unmatched versaility," Shaping the Future of Spinal Instrumentation, Danek Group, Inc., 1992, p. 3. Author unknown.

*Primary Examiner*—Stephen C. Pellegrino
*Assistant Examiner*—Guy Tucker
*Attorney, Agent, or Firm*—Woodard, Emhardt, Naughton, Moriarty & McNett

[57] ABSTRACT

A system for achieving reduction of curvature of the lumbar region of the spine associated with spondylolisthesis includes a hook assembly attached to vertebra L4, transverse plates affixed to vertebrae L4 and L5, and sacral plates affixed to opposite sides of the sacrum. The hooks and the plates in combination with the longitudinal plate along the posterior anterior plane in which the spinous processes lie allows for effective reduction of the curvature and secure fixation of this region of the spine. A related system for stabilizing the cervical region of the spine includes transverse plates affixed to vertebrae C3, C4, and C5. These plates in combination with a longitudinal plate allows for effective stabilization. The transverse plates include textured surfaces that allow them to mate in a manner which prevents undesirable slippage therebetween. The system is also compact and does not interfere with the paraspinal muscles which run along either side of the spinous processes.

20 Claims, 9 Drawing Sheets

SYSTEM FOR STABILIZING THE CERVICAL AND THE LUMBAR REGION OF THE SPINE

This application is a continuation-in-part of prior application Ser. No. 031,374 filed Mar. 11, 1993, now abandoned. The benefit of the earlier filing date is claimed under 35 U.S.C. §120.

FIELD OF THE INVENTION

The present invention relates to surgical devices and methods for reducing deformity of the spine, particularly the cervical and lumbar regions, and holding these regions of the spine while a spine fusion heals. While the invention in one embodiment is capable of reducing mild rotational deformity, it particularly relates to the reduction of spondylolisthesis. In another embodiment, the present invention is capable of stabilizing the cervical region of the spine.

BACKGROUND OF THE INVENTION

Spondylolisthesis is a condition of the spine where one vertebra segment moves forward abnormally both in flexion (rotation) and translation relative to the vertebra immediately below it. This may be due to (a) torn soft tissue restraints (ligaments, joint capsules, etc.), (b) eroded and deformed joints (degenerating spondylolisthesis), or (c) a defect in the bone between the lamina, spinal process and transverse process as one unit and the rest of the vertebrae as a second unit (spondylolytic spondylolisthesis).

When spondylolisthesis is present, the upper vertebral segment moves anteriorly in a sagittal plane both in an angular flexion, as well as a straight translational direction. Generally, treatment of spondylolisthesis corrects both types of displacement so that the flexion and translation of the upper element and the relative extension or translation of the lower element are both corrected to restore the normal lordotic alignment of the lumbar spine.

One way to treat spondylolisthesis is to reduce the deformity with a pair of longitudinal plates attached at each level S-1, L-5 and L-4 by means of pedicle screws (e.g., Roy Camille plates or variable slotted plates (Steppe plates)). Since the pedicle screws are angled medially in line with the long axis of the pedicle, the distance between the tips of the screws and the position where the screw will ultimately attach to the plate is different. Another difficulty with longitudinal plates is aligning multiple screws inserted at different pedicle angles even if no reduction is performed. A third problem is that reducing using only longitudinal plates is much weaker than reducing with two pedicle screws pre-connected with a transverse connecting plate. Longitudinal plates also place a large mass of metal over the facet joints where they restrict the ingrowth of blood vessels into the healing fusion and thus inhibit bone formation. The mass of the plates and screw attachment is also in the middle of the paraspinal muscles (instead of between the muscles) creating more dead space and scar tissue.

It is desirable to have a system for treating spondylolisthesis that provides secure fixation of the lower lumbar region of the spine and effectively reduces the accentuated curvature resulting from spondylolisthesis. Such desirable system would also include a plate design that does not interfere with the paraspinal muscles. Furthermore, it would be desirable if the system would allow for adjustment of the positional relationship between the plates and the pedicle screws so that optimum plate placement could be maintained before, during, and after reduction.

It is also desirable to have a system that provides secure fixation of the cervical region of the spine that requires treatment for conditions including degenerative oilsthesis, tumors, and trauma. As with the system described above for treatment of the lower lumbar region of the spine, a desirable system for treatment of the cervical region of the spine includes a plate design that does not interfere with the paraspinal muscles. Furthermore, it would be desirable if the system would allow for adjustment of a positional relationship between plates and lateral mass screws so that optimum plate placement could be maintained before, during, and after treatment.

SUMMARY OF THE INVENTION

The present invention relates to a system and the components of such a system for stabilizing a region of the spine with an anatomically correct curvature. For example, the present invention provides a system for stabilizing the lower lumbar region of the spine and for reducing displacement of vertebrae L4, L5, and the sacrum resulting from the condition known as spondylolisthesis. The system includes instrumentation that achieves the above objectives without interfering with the paraspinal muscles and permits one to maintain an optimum plate position before, during, and after reduction.

The system for treating the lower lumbar region of the spine formed in accordance with the present invention includes first and second transverse plates for securing to vertebra L4, and third and fourth transverse plates for securing to vertebra L5. The first, second, third, and fourth transverse plates each include at one end a bore for receiving a pedicle screw along a first axis. Extending from the bore in a direction transverse to the first axis are two substantially parallel spaced-apart fingers of substantially equal length. Each pair of spaced-apart fingers include a superior surface and an opposing inferior surface. The inferior surfaces of the spaced-apart fingers of the first and third transverse plates are textured and the superior surfaces of the spaced-apart fingers of the second and fourth transverse plates are textured. The system also includes first and second sacral plates that include a substantially planar body carrying a plurality of bores for rigidly fixing the sacral plates independently to opposite lateral portions of a sacrum. Extending from the body of each sacral plate are two substantially parallel spaced-apart fingers of substantially equal length having superior and opposing inferior surfaces. The inferior surfaces of the spaced-apart fingers of the first sacral plate are textured and the superior surfaces of the spaced-apart fingers of the second sacral plate are textured. A longitudinal member that includes a superior end and an inferior end connected by elongate spaced-apart members is also part of the system. The superior end, inferior end, and the spaced-apart members define a slot in the longitudinal plate. The longitudinal plate, transverse plates, and sacral plates are secured together by fasteners. The fasteners secure the spaced-apart fingers of the transverse plates and the sacral plates to the longitudinal plate.

The present invention also relates to the individual transverse plates and sacral plates that are components of the lower lumbar system described above. With respect to the transverse plates, either the inferior surface of the spaced-apart fingers or the superior surface of the spaced-apart fingers are textured with a repetitive pattern having an amplitude ranging from about 15 to about 25 thousandths of an inch. Additionally, with the transverse plates, the spaced-apart fingers may be aligned with or offset from the first axis of the bore in accordance with the present invention. With respect to the sacral plates, as with the transverse plates, either the inferior or superior surface of the spaced-apart fingers are textured with a repetitive pattern having an amplitude ranging from about 15 to about 25 thousandths of an inch.

In a specific embodiment, the present invention relates to the system described above for stabilizing the lower lumbar region of the spine and for reducing displacement of vertebrae L4, L5, and the sacrum resulting from the condition known as spondylolisthesis. In addition to first, second, third, and fourth transverse plates and the first and second sacral plates, this embodiment of the present invention includes a hook assembly for securing the longitudinal plate to a superior surface of vertebra L4. The hook assembly includes a hook that has a shaft and tip wherein the tip is positioned within the vertebral canal.

In another aspect, the present invention relates to a system for stabilizing the cervical region of the spine using instrumentation that does not interfere with the paraspinal muscles and permits one to maintain an optimum plate position before and during stabilization.

The system for stabilizing the cervical region of the spine includes first and second transverse plates for securing to vertebra C3, third and fourth transverse plates for securing to vertebra C4, and fifth and sixth transverse plates for securing to vertebra C5. The first, second, third, fourth, fifth, and sixth transverse plates each include an eye plate that includes an eye for receiving a lateral mass screw along a first axis. First, third, and fifth transverse plates are attached to the left lateral mass of vertebrae C3, C4 and C5, respectively. Second, fourth, and sixth transverse plates are attached to the right lateral mass of vertebrae C3, C4 and C5, respectively. Extending from the eye plate in a substantially medial posterior direction is an intermediate plate. One end of the intermediate plate is connected to the eye plate and the other end of the intermediate plate is connected to two substantially parallel spaced-apart fingers of substantially equal length extending in a medial direction. The spaced-apart fingers include a posterior surface and an opposing anterior surface, the anterior surface of the spaced-apart fingers of the first, third, and fifth transverse plates being textured and the posterior surface of the spaced-apart fingers of the second, fourth, and sixth transverse plates being textured. A longitudinal member that includes a superior end and an inferior end connected by two elongate spaced-apart members is also part of the system. Superior end, inferior end, and spaced-apart members define a slot in the longitudinal plate. Fasteners are passed through slots in the longitudinal plate and the transverse plates to secure them together.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
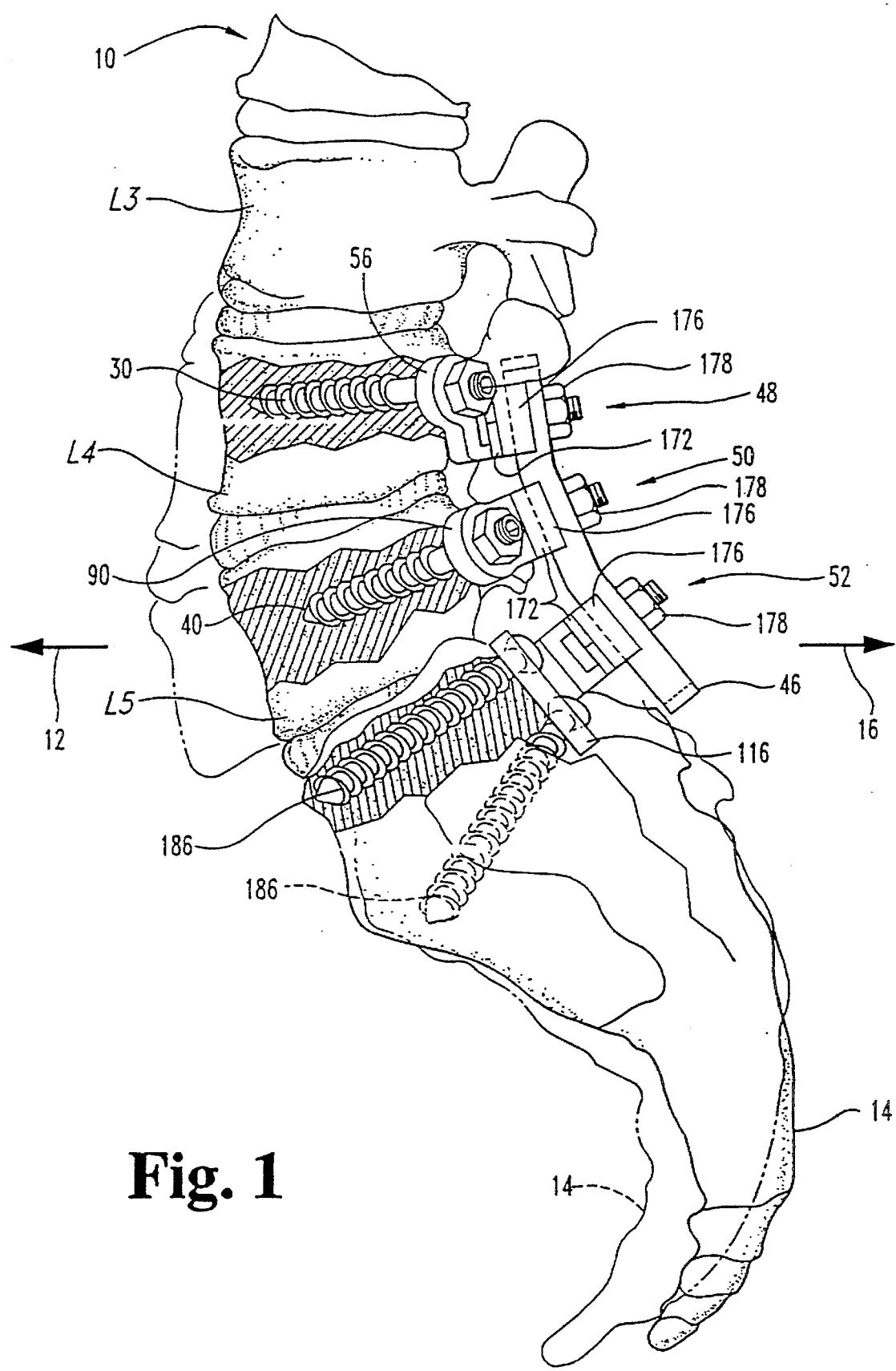
FIG. 1 is an elevational view of the left side of vertebrae L4, L5, and the sacrum with portions of the same being cut away.

Referring to the ghost line depiction in FIG. 1, spondylolisthesis is a condition of the lumbar region of spine 10 wherein the spinous process, lamina, and inferior articular processes of the fifth lumbar vertebra (and sometimes the fourth lumbar vertebra) are united together, but separate from the rest of the bone. This condition results in an accentuated curvature in an anterior direction (indicated by arrow 12) of the lumbar region of the spine and displacement of the sacrum in a posterior direction (indicated by arrow 16). As described above, correction of this curvature is achieved by pushing sacrum 14 in the anterior direction and pulling on vertebrae L4 and L5 in posterior direction 16.

Figure 2:
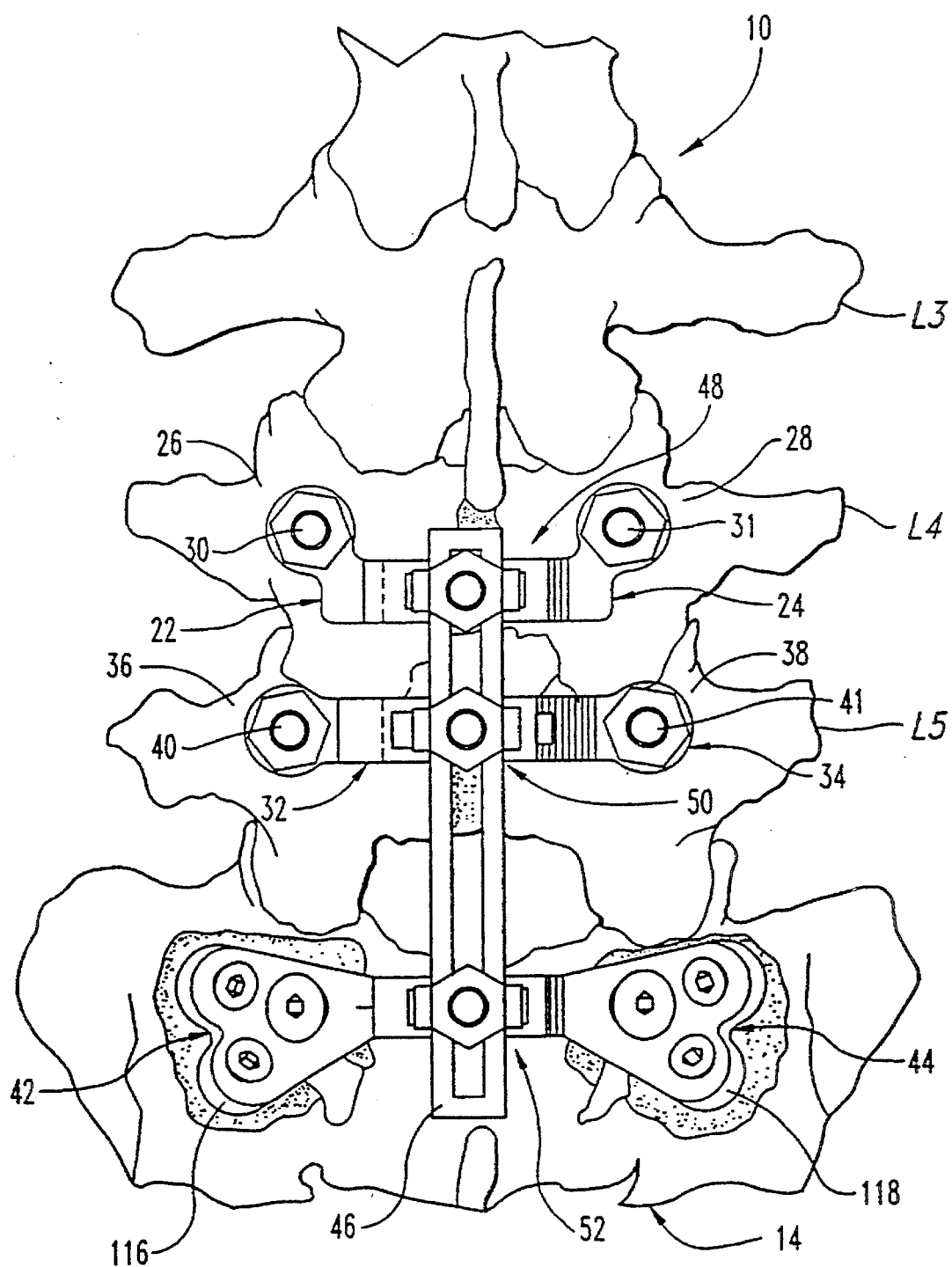
FIG. 2 is an elevational view of the posterior of the lumbar region of the spine with the system formed in accordance with the present invention applied thereto.

Referring additionally to FIG. 2, the system formed in accordance with the present invention for fixating the lumbar region of a spine 10 and reducing spondylolisthesis includes first transverse plate 22 and second transverse plate 24 that are respectively attached to left pedicle 26 and right pedicle 28 of vertebra L4 with respective pedicle screws 30 and 31. Third transverse plate 32 and fourth transverse plate 34 are respectively attached to left pedicle 36 and right pedicle 38 of vertebra L5 with respective pedicle screws 40 and 41. The system also includes first sacral plate 42 and second sacral plate 44 that are attached to sacrum 14 adjacent the lumbosacral junction on opposite lateral sides thereof. Positioned along an axis transverse to transverse plates 22, 24, 32, and 34 and sacral plates 42 and 44 is longitudinal plate 46 that is concave in the posterior direction to allow for fixation of the lower lumbar region of spine 10 in the desired position. Transverse plates 22, 24, 32, and 34 and sacral plates 42 and 44 are connected to longitudinal plate 46 by fasteners 48, 50, and 52 that are described below in more detail.

Figure 3:
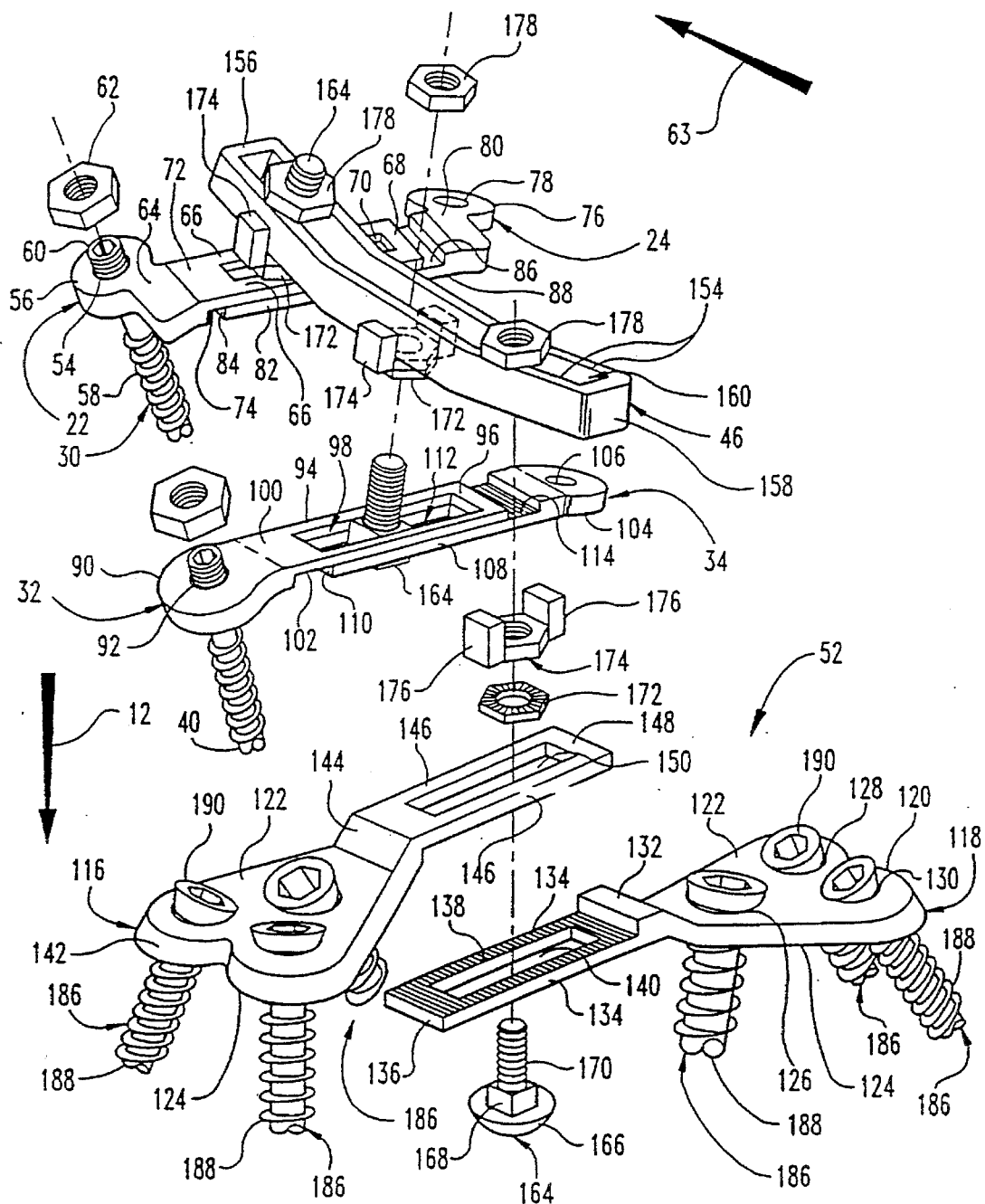
FIG. 3 is an exploded perspective view of the components of the system formed in accordance with the present invention.

Referring specifically to FIG. 3, the individual components making up the system generally described above are illustrated in more detail and described below. First transverse plate 22 includes a bore 54 at lea end 56. Left end 56 is rounded and bore 54 is centered therein and is sized to receive pedicle screw 30 along a first axis. Pedicle screw 30 includes a primary threaded portion 58 at one end for insertion into the pedicle and a secondary threaded portion 60 at the opposite end for receiving pedicle nut 62 which secures pedicle screw 30 to first transverse plate 22. Extending in the inferior direction (opposite the superior direction 63) from left end 56 is rectangular flange 64. Flange 64 provides an offset element from which elongate spaced-apart fingers 66 extend in a lateral direction substantially transverse to the first axis. Spaced-apart fingers 66 are substantially equal in length and include ends opposite flange 64 that are connected by transverse end member 68. In this manner, flange 64, spaced-apart fingers 66, and end member 68 define a slot 70 that passes through first transverse plate 22. Flange 64 is also canted laterally from right to left in the anterior direction 12 so that the plane in which left end 56 and flange 64 lie is different from the plane in which spaced-apart fingers 66 and end member 68 lie.

Left end 56 and flange 64 have a thickness D measured from posterior surface 72 to anterior surface 74. Spaced-apart fingers 66 and end member 68 have a thickness measured from posterior surface 72 and anterior surface 74 equal to about one-half D. In order to provide the narrow thickness of spaced-apart fingers 66 and end member 68, a portion of anterior surface 74 is removed. For first transverse plate 22, anterior surface 74 of spaced-apart fingers 66 and end member 68 are textured with serrations. The peaks and valleys of the serrations have a repetitive pattern having an amplitude of approximately 15 to 25 thousandths of an inch. Other repetitive patterns can be used provided they help to prevent slippage between first transverse plate 22 and second transverse plate 24 as described below in more detail. In the illustrated embodiment, first transverse plate 22 has been illustrated with an offset provided by flange 64. Alternatively, first transverse plate 22 can be straight like the third and fourth transverse plates described below in more detail.

Continuing to refer primarily to FIG. 3, second transverse plate 24 for vertebra L4 includes right end 76 that includes bore 78 and flange 80 that are substantially mirror images of left end 56, bore 54, and flange 64 of first transverse plate 22. Accordingly, these features will not be described in any more detail. Second transverse plate 24 differs from first transverse plate 22 in that spaced-apart fingers 82 and transverse end member 84 include posterior surface 86 and anterior surface 88, wherein posterior surface 86 is textured as described above. In order to provide the narrowed thickness of spaced-apart fingers 82 and end member 84, a portion of posterior surface 86 is removed. When textured posterior surface 86 of spaced-apart fingers 82 and end member 84 of second transverse plate 24 and textured anterior surface 74 of spaced-apart fingers 66 and end member 68 of first transverse plate 22 are mated together, slippage therebetween is minimized because of the mating of the textured surfaces.

Continuing to refer primarily to FIG. 3, third transverse plate 32 includes a left end 90 that is a substantially circular plate and includes bore 92 passing perpendicularly therethrough for receiving pedicle screw 40 along a first axis. Pedicle screw 40 is identical to pedicle screw 30 described above. Extending from left end 90 are substantially parallel spaced-apart fingers 94 of substantially equal length. Ends of spaced-apart fingers 94 opposite left end 90 are connected by transverse end member 96. Left end 90 is canted laterally from right to left in an anterior direction so that left end 90 lies in a plane different from a plane in which spaced-apart fingers 94 and end member 96 lie. Left end 90, spaced-apart fingers 94, and end member 96 define a slot 98 passing through third transverse plate 32. Spaced-apart fingers 94 and end member 96 have a thickness in the posterior to anterior direction approximately equal to one-half the thickness of left end 90 in the same direction. Spaced-apart fingers 94 and end member 96 include posterior surface 100 and an opposing anterior surface 102. The reduced thickness of spaced-apart fingers 94 and end member 96 is provided by removing a portion of anterior surface 102. As described above with respect to first transverse plate 22, anterior surface 102 is textured.

Continuing to refer to FIG. 3, fourth transverse plate 34 includes right end 104, that is substantially a mirror image of left end 90 of third transverse plate 32. Right end 104 includes bore 106 that passes through right end 104. Similar to left end 90 of third transverse plate 32, right end 104 is canted laterally from left to right in an anterior direction 12. Fourth transverse plate 34 also includes substantially parallel spaced-apart fingers 108 that extend laterally from right end 104. Spaced-apart fingers 108 are substantially equal in length and are connected at an end opposite right end 104 by transverse end member 110. Right end 104, spaced-apart fingers 108, and end member 110 define slot 112 passing through fourth transverse plate 34. As with third transverse plate 32, spaced-apart fingers 108 and end member 110 have a thickness in the posterior to anterior direction that is approximately equal to one-half the thickness of right end 104 in the same direction. This reduced thickness is provided by removing a portion of posterior surface 114 of spaced-apart fingers 108 and end member 110. Fourth transverse plate 34 includes spaced-apart fingers 108 whose posterior 114 is textured with the repetitive pattern described above with respect to the other transverse plates. The repetitive pattern of fourth transverse plate 34 will mate up with the repetitive third transverse plate 32 to prevent slippage therebetween.

As noted above, it should be understood that while first and second transverse plates 22 and 24 described above and illustrated in FIG. 3 include right and left ends and spaced-apart fingers that are offset, a straight-line configuration similar to third and fourth transverse plates 32 and 34 may also be applied if appropriate.

Figure 12:
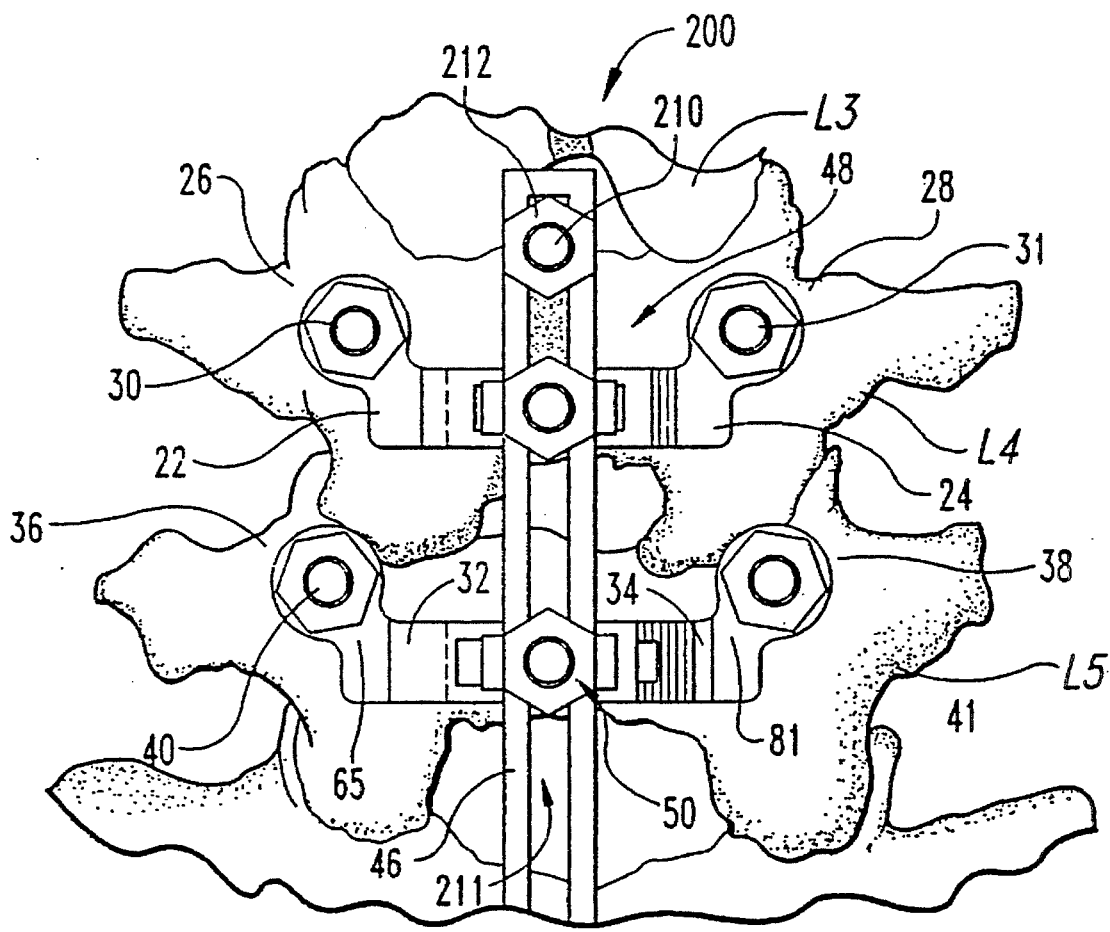
FIG. 12 is an elevational view of the posterior of the lumbar region of a spine with an alternative embodiment of the system formed in accordance with the present invention applied thereto.

Alternatively, as illustrated in FIG. 12, third and fourth transverse plates 32 and 34 may include an offset similar to first and second transverse plates 22 and 24. To achieve such offset, first transverse plate 32 is provided with substantially rectangular flange 65 between its left end and the spaced apart fingers, and fourth transverse plate 34 is provided with substantially rectangular flange 81 between its right end and the spaced apart fingers. Flanges 65 and 81 are substantially identical in shape to flanges 64 and 80 described above with respect to FIG. 3.

Figure 5:
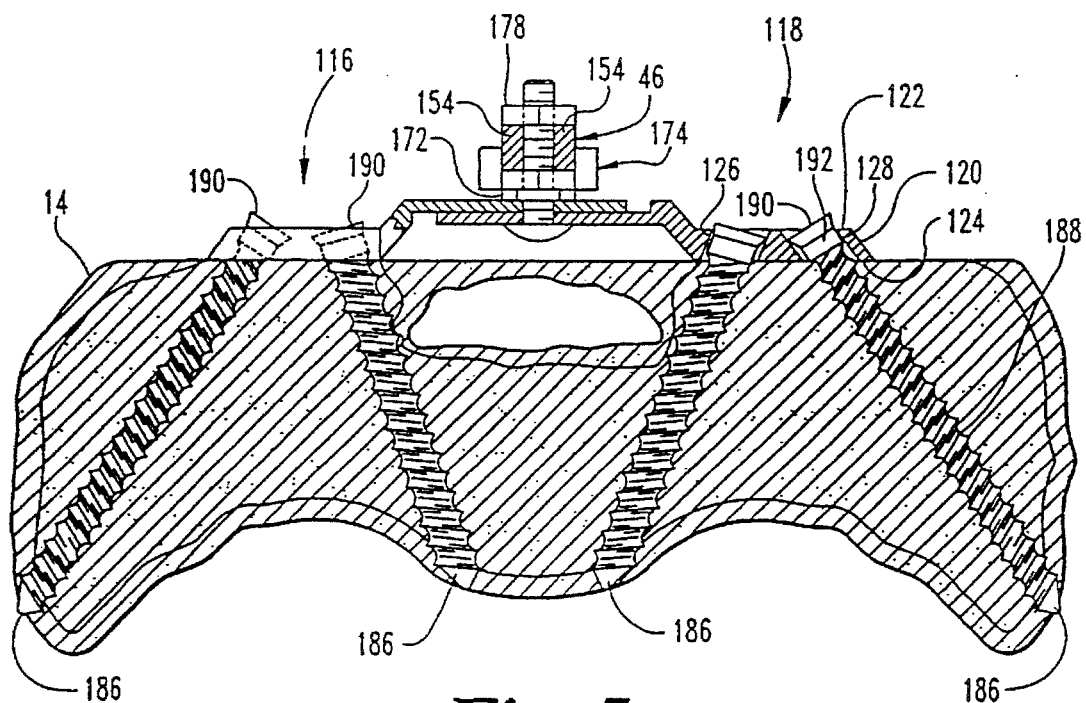
FIG. 5 is a plan view in the inferior direction of the sacrum along line 5—5 in FIG. 2.

Referring to FIGS. 2, 3, and 5, the system formed in accordance with the present invention also includes left sacral plate 116 and right sacral plate 118. In the illustrated embodiment, sacral plates 116 and 118 are illustrated as being triangulated, however, it should be understood that it is not necessary to include triangulated sacral plates and straight sacral plates including only two screws, rather than three could be used. In FIGS. 2 and 3, right sacral plate 116 and left sacral plate 118 are illustrated. Right sacral plate 118 is a mirror image of left sacral plate 116; therefore, only right sacral plate 118 will be described in detail. Right sacral plate 118 has a base 120 having a posterior surface 122 and an opposing anterior surface 124. Anterior surface 124 of sacral plate 118 is designed to intimately contact the posterior surface of the sacrum adjacent the lumbosacral joint. In position, base 120 lies in a plane generally tangential to the portion of the sacrum adjacent to the lumbosacral joint. For purposes of this description, that plane will be referred to as the sacral or dorsal plane. Base 120 of sacral plate 118 carries three bores that extend from the posterior surface of base 120 in a generally anterior direction. These bores are the pedicle bore 126, the lateral bore 128, and the oblique bore 130. The bores 126, 128, and 130, while extending in an anterior direction, are not orthogonal to the sacral plane.

Instead, the pedicle bore 126 has an axis extending in an anterior and medial direction that is offset in the medial direction preferably at an angle of about 15° to a line orthogonal to the sacral plane, although this angle may vary depending upon the particular sacral anatomy being fixed. It is understood that a screw that extends through this bore extends through the pedicle of the sacrum and must always lie within the pedicle.

Lateral bore 128 extends in an anterior and lateral direction that is preferably offset in the lateral direction at an angle of about 30° from a line orthogonal to the sacral plane. If desired, the lateral angle may be varied and the direction of the bore canted in either an inferior or superior direction relative to the sacral plane depending on the sacral anatomy.

Oblique bore 130 passes through base 120 and is offset in the lateral and inferior directions. Bore 130 when viewed in the sacral plane is first preferably offset about 45° from a lateral line, but may be varied depending on the particular sacral anatomy. The bore 130 is also offset in the lateral direction preferably about 30° from a line orthogonal to the sacral plane but, again, may be varied depending upon the particular sacral anatomy.

Extending from the left lateral side of right sacral plate 118 is flange 132. Flange 132 is substantially rectangular and has a thickness in the posterior to anterior direction substantially equal to the thickness of base 120 in the same direction. Flange 132 extends laterally from base 120, in a posterior direction from right to left at an angle of about 45° in the illustrated embodiment. Flange 132 is relatively short with respect to the length of the spaced-apart fingers described below. This angle can be varied depending on the particular sacral anatomy. Extending from the end of flange 132 opposite sacral plate 118 are substantially parallel spaced-apart fingers 134 of substantially equal length. Ends of spaced-apart fingers 134 opposite flange 132 are connected by transverse end member 136. Spaced-apart fingers 134 and end member 136 have a thickness measured in the posterior to anterior direction approximately equal to one-half the thickness of flange 132 or body 120 measured in the same direction. This reduced thickness is provided by removing a portion of the posterior surface 138 of spaced-apart fingers 134 and end member 136. Posterior surface 138 of spaced-apart fingers 134 and end member 136 is also textured with a repetitive pattern in a manner similar to first, second, third, and fourth transverse plates described above. As with the transverse plates, flange 132, end member 136, and spaced-apart fingers 138 define a slot 140 through right sacral plate 118.

Continuing to refer to FIGS. 2, 3, and 5, left sacral plate 116 includes a base 142 and flange 144 that are substantially mirror images of base 120 and flange 132 of right sacral plate 118. Extending from flange 144 are substantially parallel spaced-apart fingers 146 whose ends opposite flange 144 are connected by transverse end member 148. Spaced-apart fingers 146, end member 148, and flange 144 define slot 150 through left sacral plate 116. As with the spaced-apart fingers 134 and the end member 136 of right sacral plate 118, spaced-apart fingers 146 and end member 148 of left sacral plate 116 have a thickness measured in the posterior to anterior direction that is approximately equal to one-half the thickness of flange 144 or base 142 measured in the same direction. Spaced-apart fingers 146 and end member 148 of left sacral plate 116 include an anterior surface 124 that has a portion cut away to provide this thickness. Anterior surface 124 is also textured as described above.

Referring to FIGS. 1, 2, and 3, the illustrated system includes longitudinal plate 46 that includes two spaced-apart elongate members 154 whose inferior end and superior end are connected by transverse members 156 and 158. Transverse end members 156 and 158, and spaced-apart members 154 define a slot 160 through longitudinal plate 46. Longitudinal plate 46 is concave in the posterior direction which provides the curvature needed to successfully treat spondylolisthesis. The plate is bent on the table to the alignment desired as determined by a template bent to match the patient or the final alignment desired. Longitudinal plate 46 is long enough to extend between first transverse plate 22 and second transverse plate 24 on vertebra L4 and sacral plates 116 and 118 on the sacrum. Longitudinal plate 46 has a thickness measured in the anterior to posterior direction that is substantial enough to provide the rigidity needed for complete fixation and treatment of the spine.

Referring to primarily FIGS. 2, 3, 4, and 5, fasteners 48, 50, and 52 used to secure the transverse plates and the sacral plates to the longitudinal plate are identical except for the differences noted below. Fasteners 48, 50, and 52 include carriage bolt 164 that includes head 166, square flange 168, and threaded portion 170. Flange 168 is located between head 166 and threaded portion 170 and has a thickness that is substantially equal to the combined thickness of the spaced-apart fingers of the first and second transverse plates, or any of the other pairs of plates. Flange 168 has a square cross section orthogonal to the axis of the threaded portion. The lengths of the sides of flange 168 are slightly less than the width of the slots in the transverse plates or sacral plates. Accordingly, a square flange can be positioned within the respective slots and prevented from rotating. Threaded portion 170 is generally long enough to extend through the combined spaced-apart fingers of the respective pairs of plates, the other elements of the fastener described below in more detail, and the posterior surface of the longitudinal plate. Depending on the particular spinal anatomy, fastener 50 may include a threaded portion that is longer than the threaded portions for fasteners 48 and 52. Fasteners 48, 50, and 52 also include a thin primary nut 172 that is threaded to mate with threaded portion 170 on carriage bolt 164. Primary nut 172 includes a posterior and anterior surface, both of which are textured to facilitate secure tightening against the posterior surface of the transverse plates and to prevent slippage between nut 172 and the anterior surface of washer 174 described below. After threaded portion 170 is passed through the slots in a pair of plates, primary nut 172 and carriage bolt 164 are used to secure spaced-apart fingers of the respective pairs of plates together. Fasteners 48, 50, and 52 also include thin washer 174 that has a bore for receiving threaded portion 162 of carriage bolt 164 after primary nut 172 has been seated. Around periphery of washer 174 are two flanges 176 extending in the posterior direction. Flanges 176 are spaced-apart 180° around the periphery of washer 174. The lateral distance between flanges 176 is large enough so spaced-apart members 154 of the longitudinal plate 46 will fit between flanges 176. Flanges 176 extend from washer 174 in a posterior direction, a distance that is less than the thickness of the longitudinal plate measured in the same direction so that the ends of flanges 176 do not extend above longitudinal plate 46 when the system is secured together. After threaded portion 170 is passed through slot 160 in longitudinal plate 56, threaded portion 170 is secured by secondary nut 178 that includes a threaded bore for mating with threaded portion 170.

Figure 4:
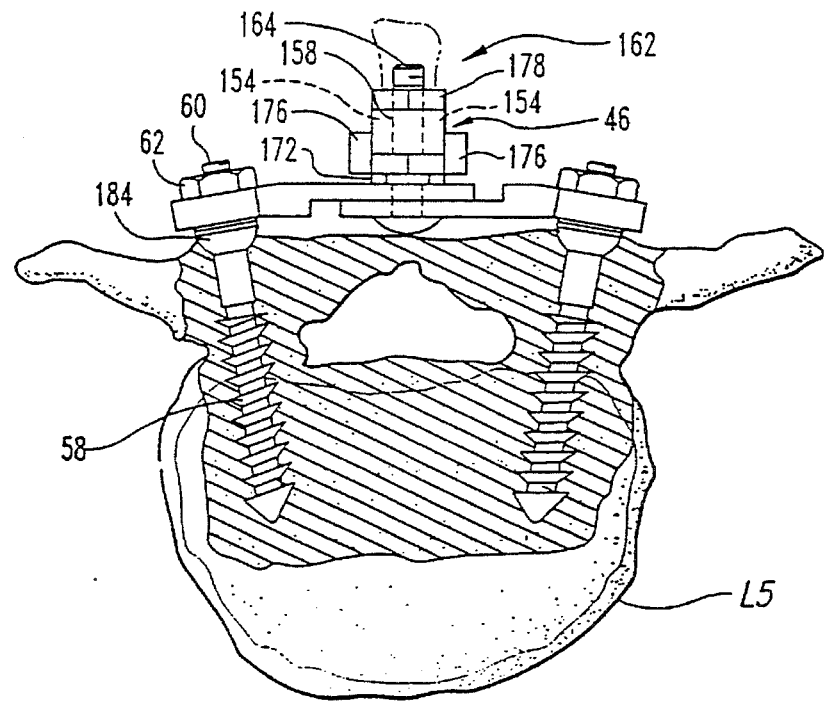
FIG. 4 is a plan view in the inferior direction of vertebra L5 along line 4—4 in FIG. 2.

Referring to FIGS. 2, 3, and 4, pedicle screws 30, 31, 40, and 41 used to secure first, second, third, and fourth transverse plates to vertebrae L4 and L5 include at a lower end a primary threaded portion 58 and at the opposite end a secondary threaded portion 60. Intermediate these threaded portions is a flange 184 having a diameter slightly larger than the diameter of secondary threaded portion 60. Flange 184 terminates at its upper end in a shoulder that is positioned in a plane orthogonal to the axis of the screw. The pedicle screws can be secured into vertebra L4 or L5 down to flange 184 after which the bore in the transverse plate is passed over the secondary threaded end 60 down to the shoulder of flange 184. The bore is sized just slightly larger than the secondary threaded portion so that the pedicle screw can reciprocate relative to and transverse to the plate, but cannot angulate relative to the screw axis when engaging the bore. A nut 62 is then threaded onto secondary threaded portion 60 and used to tighten the anterior surface of the plate against the shoulder of flange 184. A pedicle screw that can be used in the context of the present invention is available from Danek Group, Inc., Medical Division. To facilitate insertion of the pedicle screw into the pedicle, the end of the pedicle screw adjacent secondary threaded portion 60 includes an indentation for receiving a tool, such as an Allen wrench.

Referring to FIGS. 3 and 5, screws 186 used to affix sacral plates 116 and 118 to the sacrum include a lower threaded portion 188, an upper flared head 190, and a cylindrical section 192 immediately below head 190. Head 190 also carries an Allen socket so that the screw can be rotated into a hole drilled in the pedicle. The bone engaging threads on the lower threaded portion 188 are of conventional design. Cylindrical section 192 has a diameter slightly less than the diameter of the pedicle bore passing through the sacral plates. The diameters are chosen such that when cylindrical section 192 is in the bore, the screw can rotate and reciprocate. However, the tolerances are such that the screw cannot angulate or toggle relative to the axis of the bore. Upper flared head 190 is configured to mate with a countersink provided in the bore when the screw is completely threaded into the sacrum. The same screw is employed in both the lateral bore and the oblique bore.

In use, the system described above can be secured to the lower lumbar region of the spine in accordance with the following steps. It should be understood that differing procedures may be applicable for particular situations and spinal anatomies.

Referring to FIGS. 2 and 3, pedicle screws 30, 31, 40, and 41 are inserted into the pedicles of vertebrae L4 and L5 using conventional techniques. Sacral plates 116 and 118 are secured to a sacrum adjacent the lumbosacral junction with the screws described above. First transverse plate 22 and second transverse 24 plate are loosely mated together by passing threaded portion 170 of carriage bolt 164 through the slots in first plate 22 and second plate 24. The carriage bolt is loosely held in place threading thin nut 172 on exposed threaded portion 170. Bore 78 of second transverse plate 24 is slipped over secondary threaded portion 60 of right pedicle screw 31 and loosely secured thereto with a conventional nut. Bore 54 of first transverse plate 22 is then slipped over secondary threaded end 60 of left pedicle screw 30 and secured loosely thereto with conventional nut 62. Third and fourth transverse plates 32 and 34 are loosely secured to pedicle screws 40 and 41 that have been inserted to vertebra L5 in a manner similar to that described above with respect to first transverse plate 22 and second transverse plate 24.

With respect to sacral plates 116 and 118, threaded portion 170 of carriage bolt 164 is passed through slots 140 and 150 before the sacral plates are secured to the sacrum. Again, a textured nut 172 is used to loosely secure carriage bolt 164 within slots 140 and 150 of left sacral plate 116 and right sacral plate 118. Sacral plates 116 and 118 are then secured to the sacrum using screws 186. Once the transverse plates and sacral plates are secured to the respective spinal anatomy, textured nuts 172 on carriage bolts 164 can be tightened so that the textured surfaces of the respective spaced-apart fingers come in contact and prevent slippage between the respective plates. Next, flanged washer 174 is slipped over the exposed end of each of the carriage bolts 164 followed by placement of the longitudinal plate over the exposed ends of the carriage bolts. Longitudinal plate 46 is then secured to the sacral plates and the transverse plates using the secondary nuts 178 and the exposed portions of the carriage bolts.

Depending on the degree of displacement and curvature resulting from spondylolisthesis, initially the anterior side of longitudinal plate 46 may not contact washer 174 of the fastener for L5. In order to achieve reduction, this gap can be closed by tightening secondary nut 178 on carriage bolt 164. This tightening causes the system to pull on vertebrae L5 and L4 in a posterior direction while pushing on the sacrum in the anterior direction.

In applying the system described above, it should be understood that while the specific transverse plates are designed to avoid various anatomical elements of the lower region of the spine, it may be necessary to remove various anatomical elements in order to achieve placement of the system components. Alternatively, different degrees of offset between the bores for the pedicle screws and the spaced-apart fingers can be used.

In accordance with the present invention, pedicle screws are inserted into the pedicles of vertebrae L4 and L5 so that the pedicle screws are at angles that diverge from each other in the posterior direction. When longitudinal plate 46 is affixed to the carriage bolts as described above, before reduction, the distance between the diverging rays associated with the pedicle screws would be fixed, e.g., distance A. After reduction, when vertebrae L4 and L5 are brought into closer proximity with longitudinal bar, the distance between the diverging rays associated with the pedicle screws would be reduced to a distance B, which would be less than A. The system formed in accordance with the present invention provides a means for adjusting for this change in distance between the pedicle screws, which allows one to maintain an optimum plate placement with respect to the plates and the pedicle screws. As the reduction is implemented, the fasteners can be loosened by loosening nut 178 and nut 172. In this manner, the spacing between the individual plates making up the pairs of plates can be adjusted by allowing the textured surfaces to slide over each other. After the desired spacing is achieved, the nuts 172 and 178 can be tightened again to secure the plates together.

Figure 6:
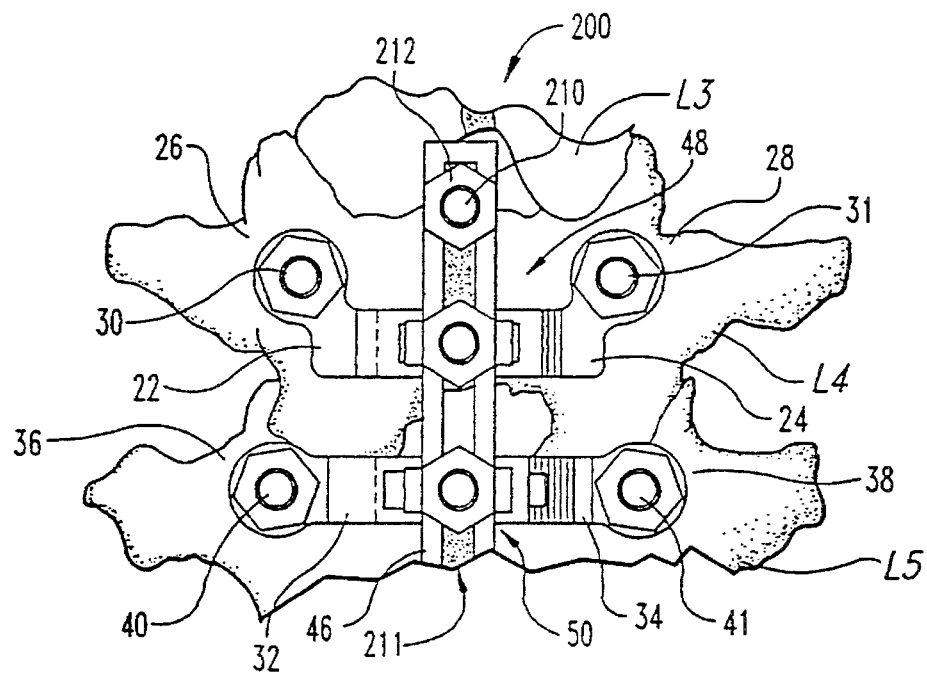
FIG. 6 is an elevational view of the posterior of the lumbar region of the spine with the lower lumbar region embodiment including the hook assembly formed in accordance with the present invention applied thereto.
Figure 7:
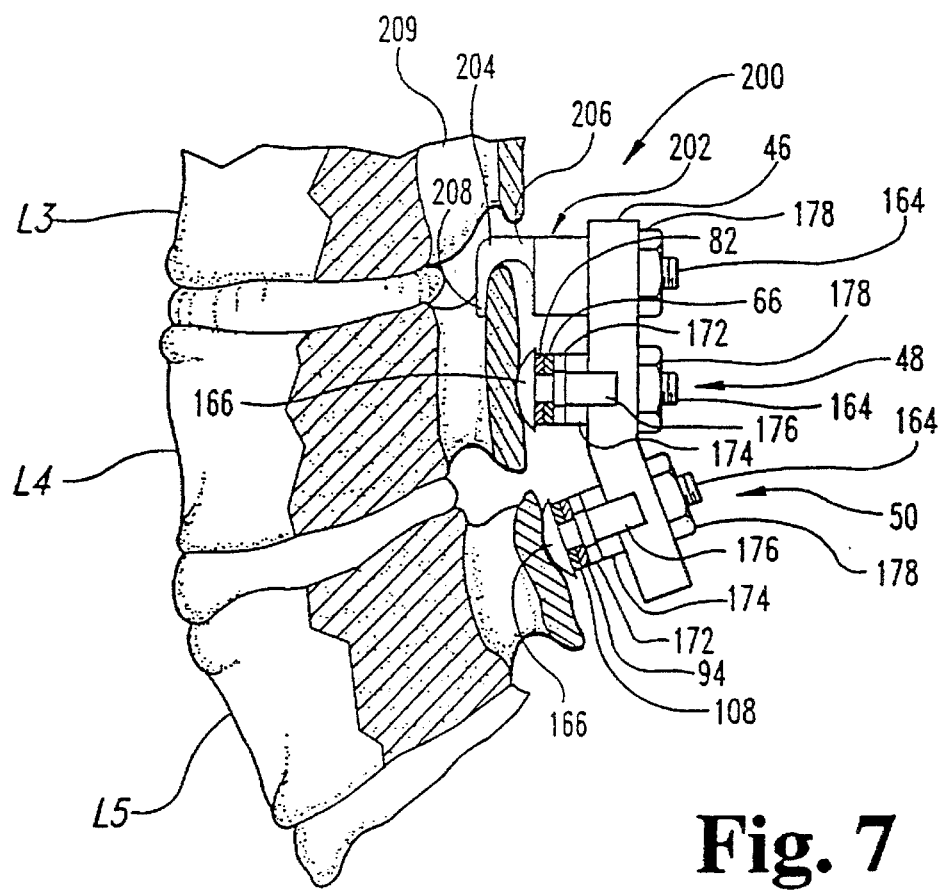
FIG. 7 is an elevational view of the lea side of the lower lumbar region of the spine of FIG. 6 with portions of the same being cut away.

Referring to FIGS. 6 and 7, if additional stabilization of the spine to longitudinal plate 46 is desired, hook assembly 200 can be employed. Biomechanically, adding a hook of hook assembly 200 to the pedicle fixation of a level significantly strengthens the fixation at that level. The hook helps prevent loosening of the screw in a pedicle and the screw(s) help prevent cutting out of the hook from the lamina. Hook assembly 200 is compatible with the transverse plates and longitudinal plates described above for stabilizing the lumbar region of the spine. Additionally, hook assembly 200 is also compatible with other combinations of transverse plates that are used to stabilize other regions of the spine. The following description of the hook assembly aspect of the present invention with reference to FIGS. 6 and 7 identifies the common elements in FIGS. 6 and 7 and FIGS. 1–5 with the same numbering for simplicity. It should be understood that, although FIGS. 1–5 and FIGS. 6 and 7 describe the present invention in the context of a system for stabilizing the lower lumbar region of the spine, the sacral plates described above can be replaced with a pair of transverse plates so that other regions of the spine can be stabilized in accordance with the present invention.

Hook assembly 200 includes hook assembly body 202. From the anterior end of hook assembly body 202 extends hook 204 that includes shaft 206 having one end connected to hook assembly body 202 and an opposite end connected to tip 208. Tip 208 is spaced apart from hook assembly body 202 a distance sufficient to enable tip 208 to extend over the superior surface of vertebra L4 so that tip 208 can be inserted into vertebral canal 209. The posterior side of hook assembly body 202 opposite hook 204 includes bolt 210 that extends in a posterior direction. Bolt 210 has a length that allows it to extend through slot 211 in longitudinal plate 46. Nut 212 is threaded onto the end of bolt 210 that extends through longitudinal plate 46 and serves to secure hook assembly 200 to longitudinal plate 46.

Figure 8:
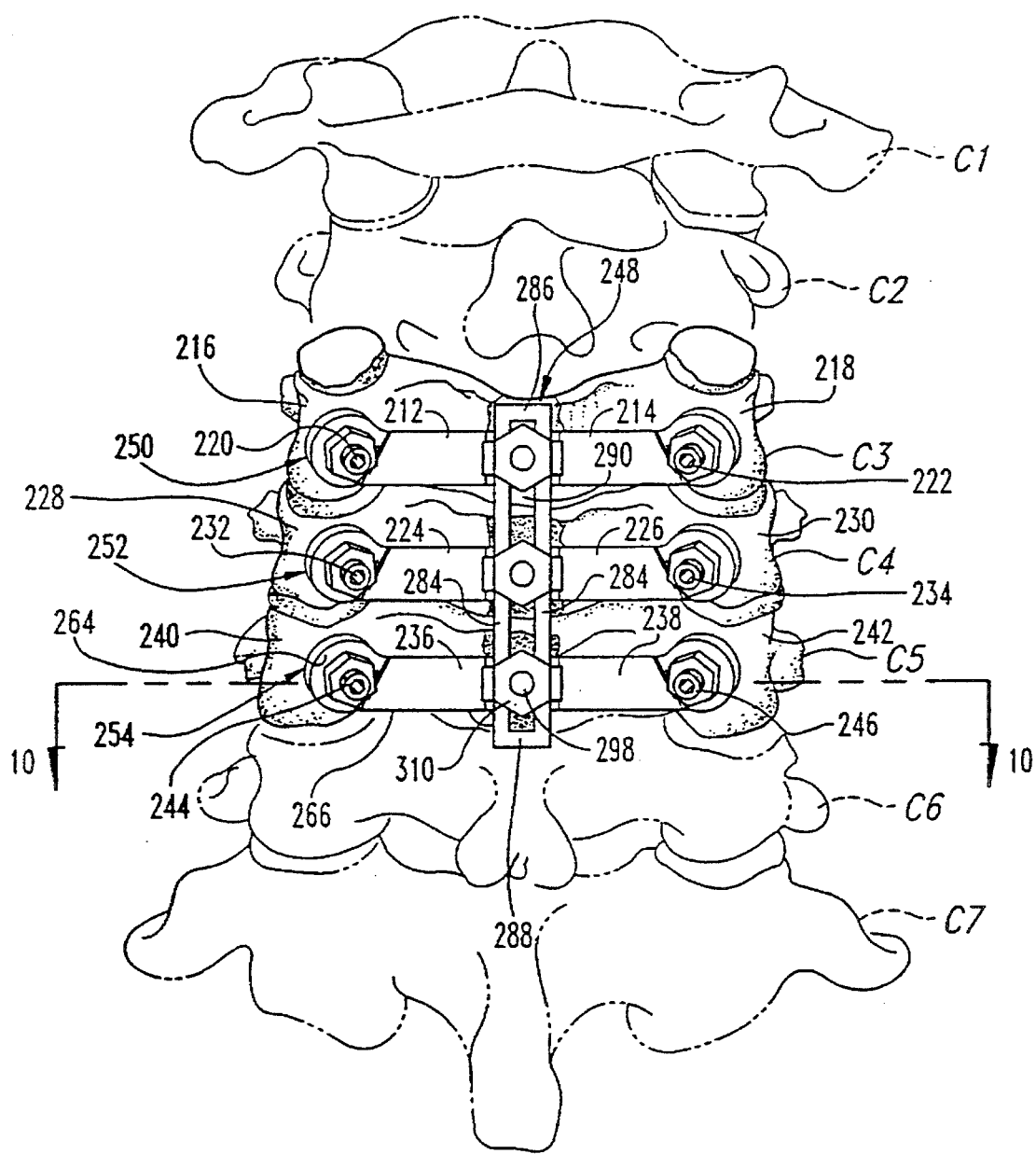
FIG. 8 is an elevational view of the posterior of the cervical region of the spine with the cervical embodiment of the system formed in accordance with the present invention applied thereto.

As noted above, in addition to stabilizing the lower lumbar region of the spine, the transverse plates and longitudinal plates formed in accordance with the present invention can be utilized to stabilize other regions of the spine. Referring to FIG. 8, transverse plates 212, 214, 224, 226, 236, and 238, longitudinal plate 248, fasteners 250, 252, and 254, and lateral mass screws 220, 222, 232, 234, 244, and 246 are used to provide a system that can stabilize the cervical region of the spine. Again, it should be understood that the following description of the stabilization of the cervical region is exemplary of systems formed in accordance with the present invention that are specifically designed to stabilize other regions of the spine.

Figure 9:
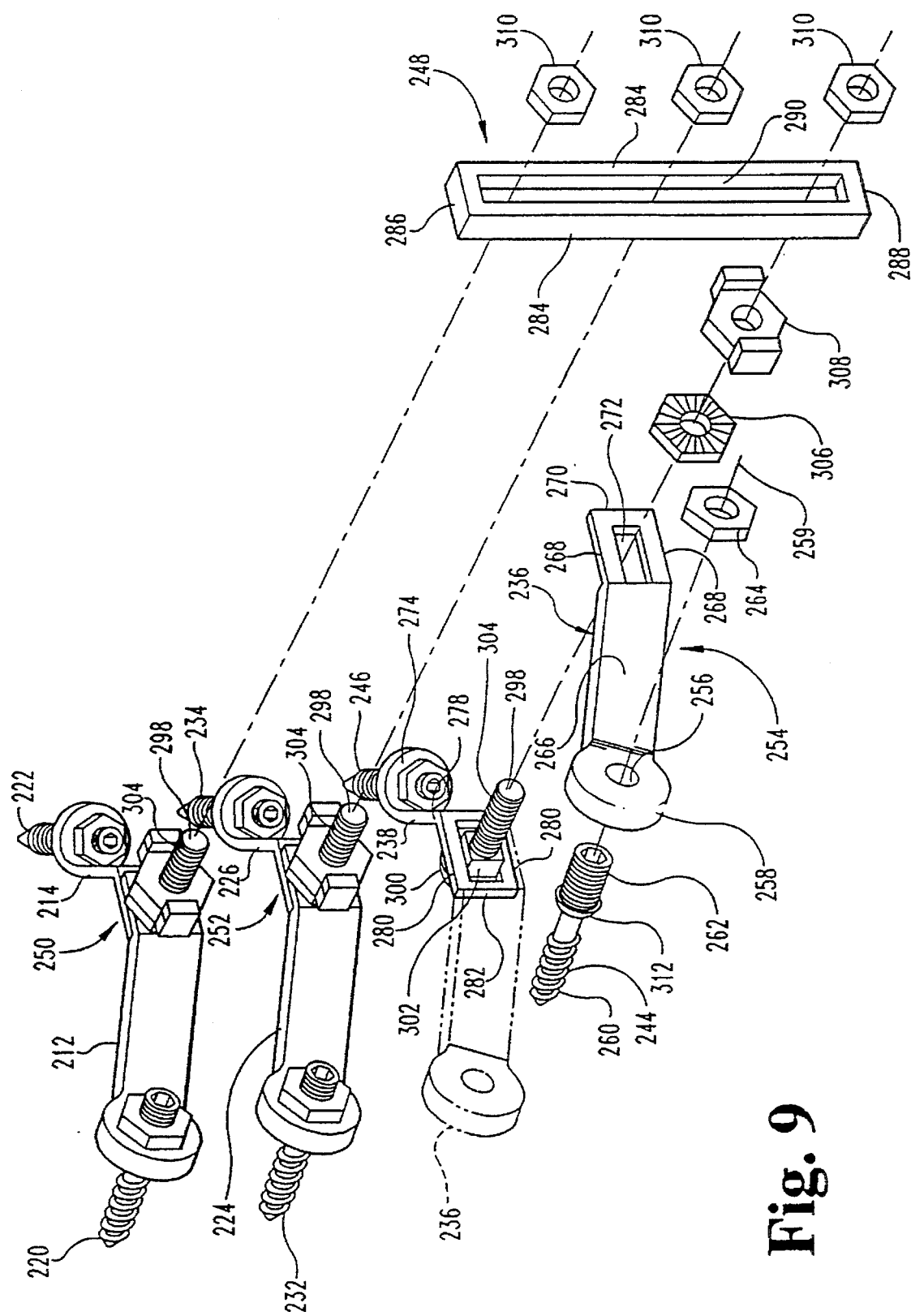
FIG. 9 is an exploded perspective view of the components of the cervical embodiment formed in accordance with the present invention.

Referring additionally to FIG. 9, the system formed in accordance with the present invention for stabilizing the cervical region of the spine includes first transverse plate 212 and second transverse plate 214 that are respectively attached to left lateral mass 216 and right lateral mass 218 of vertebra C3 with respective lateral mass screws 220 and 222. Third transverse plate 224 and fourth transverse plate 226 are respectively attached to left lateral mass 228 and right lateral mass 230 of vertebra C4 with respective lateral mass screws 232 and 234. The system also includes fifth transverse plate 236 and sixth transverse plate 238 that are attached to left lateral mass 240 and right lateral mass 242 of vertebra C5 with respective left lateral mass screw 244 and right lateral mass screw 246. Positioned along an axis transverse to transverse plates 212, 214, 224, 226, 236, and 238 is longitudinal plate 248 that in the illustrated embodiment is straight, although depending on the particular region of the spine being stabilized, longitudinal plate 248 can be concave in the posterior direction to allow for stabilization in the desired position. Transverse plates 212, 214, 224, 226, 236, and 238 are connected to longitudinal plate 248 by fasteners 250, 252, and 254 that are described below in more detail.

Referring specifically to FIG. 9, the individual components making up the cervical system generally described above are illustrated in more detail and described below in more detail. Fifth transverse plate 236 and sixth transverse plate 238, associated fastener 254, and lateral mass screws 244 and 246 are described below in detail. Fifth transverse plate 236 and sixth transverse plate 238 are described since an exploded view of these elements is provided in FIG. 9. It should be understood that the description below in the context of fifth transverse plate 236 and sixth transverse plate 238 is equally applicable to the other transverse plates and associated components. The primary difference between the respective transverse plates is the degree of canting of the eye plates of the transverse plates in the superior direction and the lateral direction.

Fifth transverse plate 236 includes an eye plate 258 at its left lateral end. Eye plate 258 is rounded on its periphery and includes eye 256 centered therein. Eye 256 passes from an anterior surface to a posterior surface of eye plate 258. Eye 256 is sized to receive left lateral mass screw 244 along a first axis 259. Left lateral mass screw 244 includes a primary threaded portion 260 at an anterior end and a secondary threaded portion 262 at an opposite posterior end. In use, primary threaded portion 260 is threaded into left lateral mass 240 and secondary threaded portion 262 is passed through eye 256 and secured to first transverse plate 212 by nut 264. Extending in a substantially medial and a substantially posterior direction from the periphery of eye plate 258 is an intermediate plate 266. Intermediate plate 266 is rectangular in shape, having a left lateral short end connected to the medial periphery of eye plate 258. The right medial end of intermediate plate 266 is positioned posteriorly and medially from the left lateral end. Elongate spaced-apart fingers 268 extend from the right medial end of intermediate plate 266 in a medial direction substantially transverse to first axis 259. Spaced-apart fingers 268 are substantially equal in length and include an end opposite intermediate flange 266 that is connected by transverse end member 270. In this manner, the right medial end of intermediate plate 266, spaced-apart fingers 268, and transverse end member 270 define a slot 272 that passes through fifth transverse plate 212. As described below in more detail, eye plate 258 can be canted laterally and in a superior direction so that first axis 259 coincides with the line along which lateral mass screw 244 is optimally inserted into left lateral mass 240 for proper and safe fixation.

Eye plate 258 and intermediate plate 266 have a thickness D measured from their posterior surface to their anterior surface. Spaced-apart fingers 268 and transverse end member 270 have a thickness measured from their posterior surface to their anterior surface that is equal to about one-half D. In order to provide the narrowed thickness of spaced-apart fingers 268 and transverse end member 270, a portion of the anterior surface of these elements is removed. For fifth transverse plate 236, the anterior surface of spaced-apart fingers 268 and transverse end member 270 are textured with setrations. In the illustrated embodiment, the peaks and valleys of the setrations have a repetitive pattern having an amplitude of approximately 15 to about 25 thousandths of an inch. Other repetitive patterns can be used provided they help to prevent slippage between fifth transverse plate 236 and sixth transverse plate 238, as described below in more detail.

In the illustrated embodiment, fifth transverse plate 236 and sixth transverse plate 238 are illustrated with eye plates 258 and 274 being canted in the left and right lateral direction, respectively, and in the superior direction. Alternatively, other degrees of canting can be used, or eye plates 258 and 270 may not be canted at all, depending upon the particular anatomical requirements.

Continuing to refer primarily to FIG. 9, sixth transverse plate 238 for vertebra C4 includes eye plate 274 that includes an eye and intermediate flange 278 that are substantially mirror images of eye plate 258, eye 256, and intermediate plate 266 of fifth transverse plate 236. Accordingly, reference is made to the earlier description for an understanding of these elements. Sixth transverse plate 238 differs from fifth transverse plate 236 in that it includes spaced-apart fingers 280 and transverse end member 282 that include a posterior surface that is textured with serrations as described above. In order to provide the narrowed thickness of spaced-apart fingers 280 and transverse end member 282, a portion of the posterior surface of these elements is removed. When the textured posterior surface of spaced-apart fingers 280 and transverse end member 282 of sixth transverse plate 238 and the textured anterior surface of spaced-apart fingers 268 and transverse end member 270 of fifth transverse plate 236 are mated together, slippage therebetween is minimized because mating of the textured surfaces tends to lock the two transverse plates together.

Continuing to refer primarily to FIG. 9, first transverse plate 212 and third transverse plate 224 are substantially identical to fifth transverse plate 236. Second transverse plate 214 and fourth transverse plate 226 are substantially identical to sixth transverse plate 238. It should be understood that the various sets of transverse plates may have differing canting of the respective eye plates to accommodate the particular anatomical configuration of the respective lateral masses. For simplicity, the reader is referred to the description of fifth transverse plate 236 and sixth transverse plate 238 for an understanding of the various structural elements of the first, second, third, and fourth transverse plates.

Still referring primarily to FIGS. 8 and 9, the system for stabilizing the cervical region of the spine formed in accordance with the present invention includes longitudinal plate 248 that includes two spaced-apart elongate members 284 whose inferior end and superior end are connected by transverse members 286 and 288. Transverse end members 286 and 288 and spaced-apart members 284 define a slot 290 through longitudinal plate 248. Longitudinal plate 248 in the illustrated embodiment is straight; however, it should be understood that longitudinal plate 248 can be concave in the posterior direction in order to provide the curvature needed to successfully treat the spine. If longitudinal plate 248 is to be bent, it can be bent on the table to the alignment desired as determined by a template bent to match the patient or the final alignment desired. Longitudinal plate 248 is long enough to extend between first transverse plate 212 and second transverse plate 214 on vertebra C3 and fifth transverse plate 236 and sixth transverse plate 238 on vertebra C5. Longitudinal plate 248 has a thickness measured in the anterior-to-posterior direction that is substantial enough to provide the rigidity needed for complete stabilization and treatment of the spine.

Figure 10:
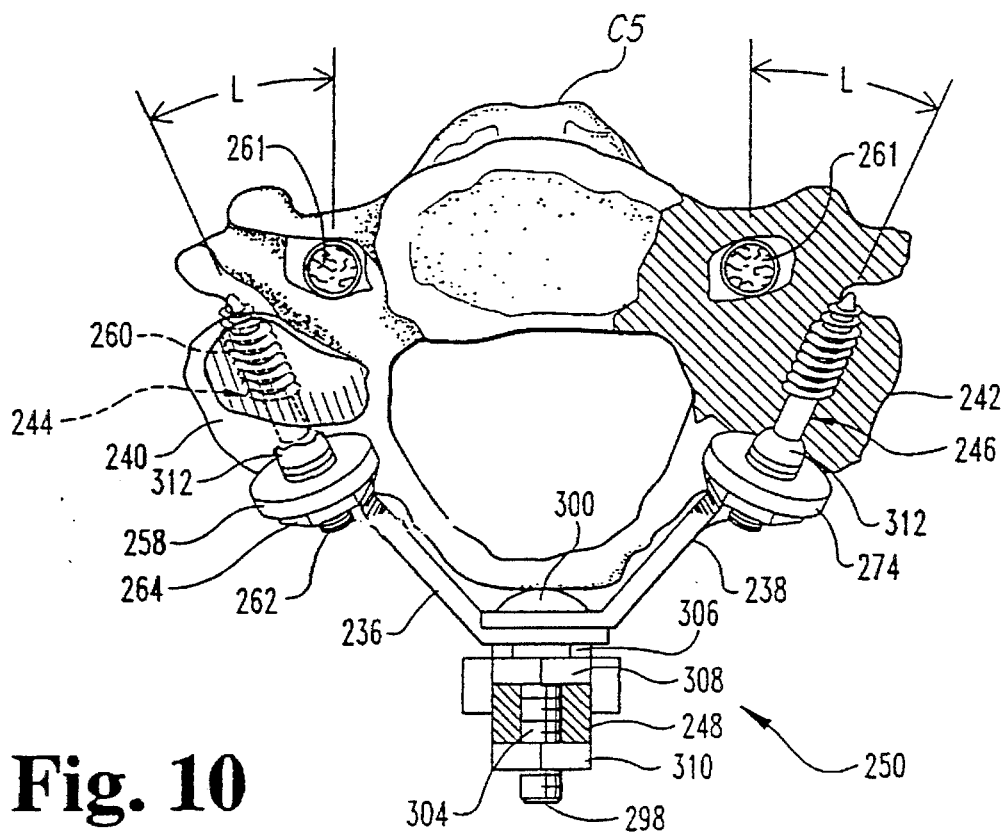
FIG. 10 is a plan view in the inferior direction of vertebra C4 along line 10—10 in FIG. 8.
Figure 11:
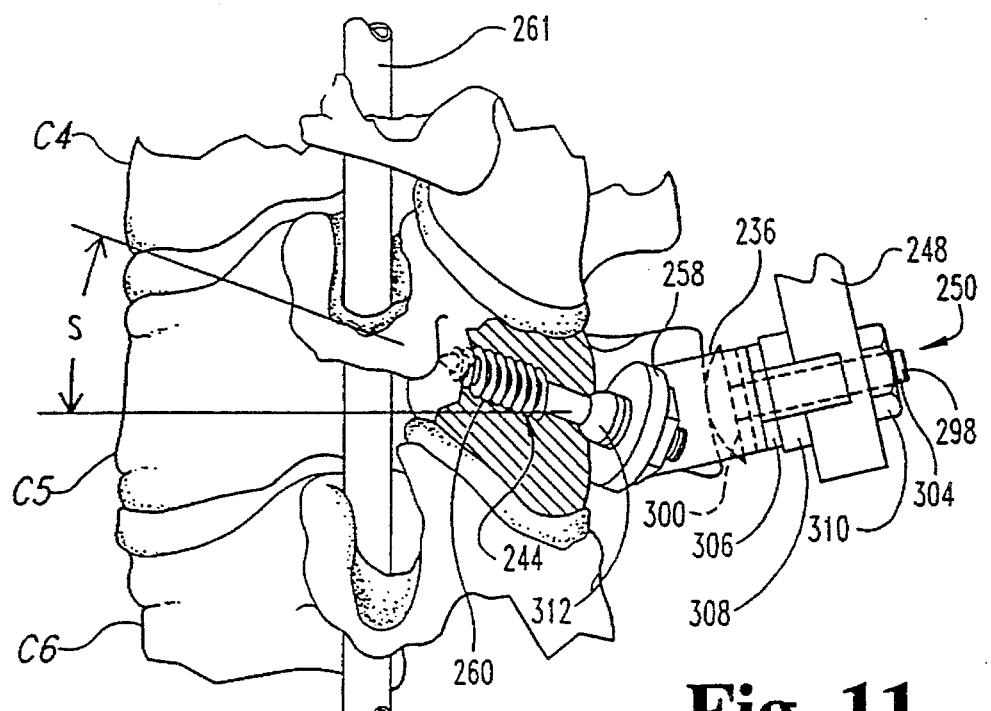
FIG. 11 is an elevational view of the left side of vertebrae C4, C5, and C6 of FIG. 8 with portions of the same being cut away.

Referring additionally to FIGS. 10 and 11, fastener 250 for first transverse plate 212 and second transverse plate 214, fastener 252 for third transverse plate 224 and fourth transverse plate 226, and fastener 254 for fifth transverse plate 236 and sixth transverse plate 238 are used to secure the respective pairs of transverse plates to longitudinal plate 248. Fasteners 250, 252, and 254 are substantially identical to fasteners 48, 50, and 52 described above with reference to FIGS. 2, 3, 4, and 5. Fasteners 250, 252, and 254 each include carriage bolt 298, that includes head 300 and square range 302 on one end, and threaded portion 304 on another end. Carriage bolt 298, including head 300, square flange 302, and threaded portion 304 are substantially identical to carriage bolt 164, that includes head 166, square flange 168, and threaded portion 170 described above with reference to fasteners 48, 50, and 52 in FIGS. 2, 3, 4, and 5. For simplicity, a detailed description of these elements is not provided at this point, and the reader is referred to the earlier description. Fasteners 250, 252, and 254 also include thin primary nut 306, thin washer 308, and secondary nut 310 that are substantially identical to thin primary nut 172, thin washer 174, and secondary nut 178 described above with respect to fasteners 48, 50, and 52. For purposes of full disclosure, the reader is referred to the previous description of these elements.

Referring to FIGS. 8, 9, 10, and 11, lateral mass screws 220, 222, 232, 234, 244, and 246 are used to secure first, second, third, fourth, fifth, and sixth transverse plates to respective vertebrae C3, C4, and C5. Since each of the lateral mass screws is identical, only lateral mass screw 244 will be described below. Lateral mass screw 244, as described above, includes at one end a primary threaded portion 260 and at an opposite end a secondary threaded portion 262. Primary threaded portion 260 includes threads designed to firmly secure lateral mass screw 244 in the left lateral mass of vertebra C5. Between primary threaded portion 260 and secondary threaded portion 262, lateral mass screw 244 includes shoulder 312 that is sized so that it cannot pass through eye 256 in fifth transverse plate 236. Shoulder 312 is located adjacent to the end of secondary threaded portion 262 that is closest to primary threaded portion 260. Secondary threaded portion 262 has a diameter such that it can pass through eye 256. The end of lateral mass screw 244 opposite primary threaded portion 260 includes a notch for receiving a tool, such as an Alien wrench, for rotating lateral mass screw 244. Eye 256 is sized just slightly larger than the secondary threaded portion 262 so that left lateral mass screw 244 can reciprocate relative to and transverse to fifth transverse plate 236, but cannot angulate relative to the screw axis when engaging eye 256. A lateral mass screw that can be used in the context of the present invention is available from Danek Group, Inc., Medical Division. In use, it is preferred that, prior to insertion of left lateral mass screw 244 into left lateral mass 240, a bore having a diameter smaller than the diameter of the primary threaded portion 260 of left lateral mass screw 244 is drilled into the left lateral mass 240 in accordance with accepted surgical practice. After the bore is drilled into the left lateral mass 240, left lateral mass screw 244 can be threaded into the bore using an Allen wrench inserted into the notch in the end of lateral mass screw 244. Lateral mass screw 244 has a length measured from its anterior end to the anterior side of shoulder 312 that is short enough so that when lateral mass screw 244 is seated into lateral mass 240 down to shoulder 312, primary threaded portion does not exit an opposite side of lateral mass 240. Lateral mass screw 244 can then be secured to eye plate 258 by passing secondary threaded portion 262 through eye 256 and threading nut 264 onto secondary threaded portion 262.

Continuing to refer to FIGS. 8, 9, 10, and 11, in order to avoid trauma to vertebral artery 261 and to allow complete penetration safely through left lateral mass 240, left lateral screw 244 is angled into left lateral mass 240 at a lateral angle L of approximately 20°–30° and a superior angle S of approximately 10° to 20°.

In use, the system for stabilizing the cervical region of the spine described above can be secured to the cervical region of the spine in accordance with the steps that are described below. It should be understood that differing procedures may be applicable for specific cases and spinal anatomies.

Referring to FIGS. 8, 9, 10, and 11, lateral mass screws 220, 222, 232, 234, 244, and 246 are inserted into the respective lateral masses of vertebrae C3, C4, and C5 as described above. First transverse plate 212 and second transverse plate 214 are loosely mated together by passing the threaded portion of carriage bolt 298 through the slot between the elongate spaced-apart fingers. Carriage bolt 298 is loosely held in place by threading the thin primary nut on the exposed threaded portion. The eye of second transverse plate 214 is slipped over the secondary threaded portion of right lateral mass screw 222 and loosely secured thereto with a conventional nut. The eye of first transverse plate 212 is then slipped over the secondary threaded end of left lateral mass screw 220 and secured loosely thereto with a conventional nut. Third transverse plate 224 and fourth transverse plate 226 are loosely mated together using fastener 252 as described above. Third transverse plate 224 and fourth transverse plate 226 are then loosely secured to left lateral mass screw 232 and right lateral mass screw 234 as described above with respect to first transverse plate 212, second transverse plate 214, and lateral mass screws 220 and 222. Fifth transverse plate 236 and sixth transverse plate 238 are also loosely mated together using fastener 252 as described above. Fifth transverse plate 236 and sixth transverse plate 238 are then loosely secured to left lateral mass screw 244 and right lateral mass screw 256 in a manner similar to that described above with respect to the other transverse plates. Once each set of the transverse plates is secured to the respective vertebrae, the nuts on the carriage bolts can be tightened so that the textured surfaces of the respective spaced-apart fingers come in contact with and prevent slippage between the respective plates. Next, the thin washer with flanges is slipped over the exposed threaded end of each of the carriage bolts followed by placement of the longitudinal plate over the exposed ends of the carriage bolts. The longitudinal plate is then secured to the transverse plates using conventional nuts and the exposed portions of the carriage bolts.

As noted above, it should be understood that while the specific transverse plates are designed to avoid various anatomical elements of the cervical region of the spine, it may be necessary to remove various anatomical elements in order to achieve placement of the system components. Alternatively, different degrees of offset between the eyes for the lateral mass screws and the angling of the intermediate plates and spaced-apart fingers can be used.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for stabilizing the lumbar region of the spine and reducing displacement of the spine resulting from spondylolisthesis comprising:

first and second transverse plates for securing to vertebra L4;

third and fourth transverse plates for securing to vertebra L5, said first, second, third, and fourth transverse plates each including at one end an eye plate that includes an eye for receiving a bone engaging fastener along a first axis and extending from the eye plate two substantially parallel spaced-apart fingers of substantially equal length, said spaced-apart fingers including a posterior surface and an opposing anterior surface, the anterior surface of said spaced-apart fingers of said first and third transverse plates being textured and the posterior surface of said spaced-apart fingers of said second and fourth transverse plates being textured, wherein the anterior surface of said spaced-apart fingers of said first and third transverse plates face the posterior surface of said spaced apart fingers of said second and fourth transverse plates, respectively;

first and second sacral plates, said sacral plates each including a substantially planar body having a plurality of bores for rigidly fixing said sacral plates independently to opposite lateral portions of a sacrum, extending from each body are two spaced-apart fingers of substantially equal length having posterior and opposing anterior surfaces, the anterior surface of the spaced-apart fingers of said first sacral plate being textured and the posterior surface of the spaced-apart fingers of said second sacral plate being textured, wherein the anterior surface of the spaced-apart fingers of said first sacral plate face the posterior surface of the spaced apart fingers of the second sacral plate;

longitudinal member including a superior end and an inferior end connected by spaced-apart members, said superior and inferior end and said spaced-apart members defining a slot in said longitudinal member;

a first fastener for securing the first and second transverse plates to one another and to the longitudinal member, the first fastener extending between the spaced-apart fingers of the first and second transverse plates and between the spaced-apart members of the longitudinal member when fastened;

a second fastener for securing the third and fourth transverse plates to one another and to the longitudinal member, the second fastener extending between the spaced-apart fingers of the third and fourth transverse plates and between the spaced-apart members of the longitudinal member when fastened;

a third fastener for securing the first and second sacral plates to one another and to the longitudinal member, the third fastener extending between the spaced-apart fingers of the first and second sacral plates and between the spaced-apart members of the longitudinal member; and a hook assembly for securing to vertebra L3 and said longitudinal member.

2. The system of claim 1, wherein the textured surfaces of said spaced-apart fingers include a repetitive pattern having an amplitude sufficient to prevent slippage between the textured surfaces when secured together by said fasteners.

3. The system of claim 1, wherein a longitudinal centerline runs parallel to and between the spaced-apart fingers of said first and second transverse plates, said first axis being offset from said centerline such that said longitudinal centerline does not intersect said first axis.

4. The system of claim 1, wherein a longitudinal centerline runs parallel to and between the spaced-apart fingers of said third and fourth transverse plates, said first axis being offset from said centerline such that said centerline does not intersect said first axis.

5. The system of claim 1, wherein said hook assembly comprises a hook and a threaded member, said hook and said threaded member extending from opposites sides of a hook assembly body, said hook opening in an inferior direction.

6. The system of claim 5, wherein the hook includes a tip and a shaft, the shaft extending from the hook assembly body and the tip extending from the shaft at an end opposite the hook assembly body.

7. The system of claim 6, wherein the tip is spaced apart from the hook assembly body a distance sufficient to enable the hook to be positioned over the superior surface of the vertebra with the tip in the vertebral canal.

8. A system for stabilizing the lumbar region of the spine and reducing displacement of the spine resulting from spondylolisthesis comprising:

first and second transverse plates for securing to vertebra L4;

third and fourth transverse plates for securing to vertebra L5, said first, second, third, and fourth transverse plates each including at one end an eye plate that includes an eye for receiving a pedicle screw along a first axis and extending from the eye plate two substantially parallel spaced-apart fingers of substantially equal length, said spaced-apart fingers including a posterior surface and an opposing anterior surface, the anterior surface of said spaced-apart fingers of said first and third transverse plates being textured and the posterior surface of said spaced-apart fingers of said second and fourth transverse plates being textured;

first and second sacral plates, said sacral plates each including a substantially planar body having a plurality of bores for rigidly fixing said sacral plates independently to opposite lateral portions of a sacrum, extending from each body are two spaced-apart fingers of substantially equal length having posterior and opposing anterior surfaces, the anterior surface of the spaced-apart fingers of said first sacral plate being textured and the posterior surface of the spaced-apart fingers of said second sacral plate being textured;

longitudinal member including a superior end and an inferior end connected by spaced-apart members, said superior and inferior end and said spaced-apart members defining a slot in said longitudinal member;

fasteners for securing the spaced-apart fingers of said first, second, third and fourth traverse plates, and the spaced-apart fingers of said first and second sacral plates to said longitudinal member;

a hook assembly for securing to vertebra L3 and said longitudinal member;

wherein the fasteners comprise:

a carriage bolt that includes a head, a flange for fitting into said slot, and a thread portion, said flange located between said head and said threaded portion and having a thickness substantially equal to the combined thickness in a posterior to anterior direction of the spaced-apart fingers of said first and second transverse plates;

a primary nut including a textured posterior surface and an opposing textured anterior surface;

a washer, said washer including an annular body with an outer perimeter and two opposing flanges extending in a posterior direction from opposite edges on the outer perimeter of said washer; and a secondary nut.

9. A system for stabilizing the spine comprising:

first and second transverse plates for securing to a first vertebra;

third and fourth transverse plates for securing to a second vertebra;

fifth and sixth transverse plates for securing to a third vertebra, said first, second, third, fourth, fifth, and sixth transverse plates each including at one end an eye plate that includes an eye for receiving a screw along a first axis, extending from the eye plate in a substantially medial direction is an intermediate plate, one end of the intermediate plate connected to the eye plate and another end of the intermediate plate connected to two substantially parallel spaced-apart fingers of substantially equal length extending in a medial direction substantially transverse to the first axis, said spaced-apart fingers including a posterior surface and an opposing anterior surface, the anterior surface of said spaced-apart fingers of said first, third, and fifth transverse plates being textured and the posterior surface of said spaced-apart fingers of said second, fourth, and sixth transverse plates being textured, wherein the anterior surface of said spaced-apart fingers of said first, third and fifth transverse plates face the posterior surface of said spaced-apart fingers of said second, fourth and sixth transverse plates, respectively;

longitudinal member including a superior end and an inferior end connected by spaced-apart members, said superior and inferior end and said spaced-apart member defining a slot in said longitudinal member;

a first fastener for securing the first and second transverse plates to one another and to the longitudinal member, the first fastener extending between the spaced-apart fingers of the first and second transverse plates and between the spaced-apart members of the longitudinal member when fastened;

a second fastener for securing the third and fourth transverse plates to one another and to the longitudinal member, the second fastener extending between the spaced-apart fingers of the third and fourth transverse plates and between the spaced-apart members of the longitudinal member when fastened; and a third fastener for securing the fifth and sixth transverse plates to one another and to the longitudinal member, the third fastener extending between the spaced-apart fingers of the fifth and sixth transverse plates and between the spaced-apart members of the longitudinal member.

10. The system of claim 9, wherein the textured surfaces of said spaced-apart fingers include a repetitive pattern having an amplitude sufficient to prevent slippage between the textured surfaces when secured together by said fasteners.

11. The system of claim 9, wherein the first axis is angled in a substantially superior direction and in a substantially lateral direction.

12. The system of claim 11, wherein the eye plate includes an anterior surface and an opposing posterior surface, the anterior surface and the posterior surface being substantially perpendicular to the first axis.

13. The system of claim 9, further comprising a hook assembly for securing to the first vertebra and said longitudinal member.

14. The system of claim 9, wherein the first axis is angled in a substantially inferior direction and in a substantially medial direction.

15. A system for stabilizing the spine comprising:

first and second transverse plates for securing to a first vertebra;

third and fourth transverse plates for securing to a second vertebra;

fifth and sixth transverse plates for securing to a third vertebra, said first, second, third, fourth, fifth and sixth transverse plates each including at one end an eye plate that includes an eye for receiving a screw along the first axis, extending from the eye plate in a substantially redial direction is an intermediate plate, one end of the intermediate plate connected to the eye plate and another end of the intermediate plate, connected to two substantially parallel spaced-apart fingers of substantially equal length extending in a medial direction substantially transverse to the first axis, said spaced-apart fingers including a posterior surface and an opposing surface, the anterior surface of said spaced-apart fingers of said first, third and fifth transverse plates being textured and the posterior surface of said spaced-apart fingers of second, fourth and sixth transverse plates being textured;

longitudinal member including a superior end and inferior end connected by spaced-apart members, said superior and inferior end and said spaced-apart members defining a slot in said longitudinal plates;

fasteners for securing the spaced-apart fingers of said first, second, third, fourth, fifth and sixth transverse plates to said longitudinal members;

wherein the fasteners comprise:

a carriage bolt that includes a head, a flange for fitting into said slot, and a threaded portion, said flange located between said head and said threaded portion and having a thickness substantially equal to the combined thickness in a posterior to anterior direction of the spaced-apart fingers of said first and second transverse plates;

a primary nut including a textured posterior surface and an opposing textured anterior surface;

a washer, said washer including an annular body with an outer perimeter and two opposing flanges extending in a posterior direction from opposite edges on the outer perimeter of said washer; and a secondary nut.

16. A system for stabilizing the cervical region of the spine comprising:

first and second transverse plates for securing to vertebra C3;

third and fourth transverse plates for securing to vertebra C4;

fifth and sixth transverse plates for securing to vertebra C5, said first, second, third, fourth, fifth and sixth transverse plates each including at one end an eye plate that includes an eye for receiving a lateral mass screw along a first axis, extending from the eye plate in a substantially medial posterior direction is an intermediate plate, one end of the intermediate plate connected to the eye plate and another end of the intermediate plate connected to two substantially parallel spaced-apart fingers of substantially equal length extending in a medial direction substantially transverse to the first axis, said spaced-apart fingers including a posterior surface and an opposing anterior surface, the anterior surface of said spaced-apart fingers of said first, third, and fifth transverse plates being textured and the posterior surface of said spaced-apart fingers of second, fourth and sixth transverse plates being textured, wherein the anterior surface of said spaced-apart fingers of said first, third and fifth transverse plates face the posterior surface of said spaced-apart fingers of said second, fourth and sixth transverse plates, respectively;

longitudinal member including a superior end and an inferior end connected by spaced-apart members, said superior and inferior end and said spaced-apart members defining a slot in said longitudinal member;

a first fastener for securing the first and second transverse plates to one another and to the longitudinal member, the first fastener extending between the spaced-apart fingers of the first and second transverse plates and between the spaced-apart members of the longitudinal member when fastened;

a second fastener for securing the third and fourth transverse plates to one another and to the longitudinal member, the second fastener extending between the spaced-apart fingers of the third and fourth transverse plates and between the spaced-apart members of the longitudinal member when fastened; and a third fastener for securing the fifth and sixth transverse plates to one another and to the longitudinal member, the third fastener extending between the spaced-apart fingers of the fifth and sixth transverse plates and between the spaced-apart members of the longitudinal member.

17. A system for stablilzing the lumbar region of the spine and reducing displacement of the spine resulting from spondylolisthesis, comprising:

a first transverse plate adapted for connection to a left portion of a first vertebra, the first transverse plate including a first slot therein;

a second transverse plate adapted for connection to a right portion of the first vertebra, the second transverse plate including a second slot therein;

a third transverse plate adapted for connection to a left portion of a second vertebra, the third transverse plate including a third slot therein;

a fourth transverse plate adapted for connection to a right portion of the second vertebra, the fourth transverse plate including a fourth slot therein;

a longitudinal member having a longitudinal slot defined therein;

a first fastener for securing the first and second transverse plates to one another and to the longitudinal member, the first fastener passing through the first, second, and longitudinal slots when fastened;

a second fastener for securing the third and fourth transverse plates to one another and to the longitudinal member, the second fastener passing through the third, fourth, and longitudinal slots when fastened; and a hook assembly for securing to a third vertebra and said longitudinal member;

wherein the first and second transverse plates include respective first and second textured surfaces, the first and second textured surfaces adapted to engage one another when the first fastener is fastened; and wherein the third and fourth transverse plates include respective third and fourth textured surfaces, the third and fourth textured surfaces adapted to engage one another when the second fastener is fastened.

18. The system of claim 17, wherein the first, second, third and fourth textured surfaces include a repetitive pattern having an amplitude sufficient to substantially prevent slippage between engaged textured surfaces when fastened together by the first and second fasteners.

19. The system of claim 17, further comprising:
a first sacral plate adapted for connection to a left pedicle of a sacrum, the first sacral plate including a fifth slot therein;
a second sacral plate adapted for connection to a right pedicle of the sacrum, the second sacral plate including a sixth slot therein; and
a third fastener for securing the first and second sacral plates to one another and to the longitudinal member, the third fastener passing through the fifth, sixth, and longitudinal slots when fastened.

20. The system of claim 17, wherein the first fastener comprises:
a first carriage bolt that includes a first head, a first flange for fitting into the first and second slots, and a first threaded portion, the first flange located between the first head and the first threaded portion and having a thickness substantially equal to a combined thickness of the first and second transverse plates;
a first primary nut;
a first washer, the first washer including an annular body having a surface, and two opposing flanges extending in a direction perpendicular to the surface; and
a first secondary nut.

* * * * *